US 8,121,683 B2

(12) United States Patent
Bucher et al.

(10) Patent No.: US 8,121,683 B2
(45) Date of Patent: Feb. 21, 2012

(54) EXTERNAL AUTOMATIC DEFIBRILLATOR

(75) Inventors: Heinz Bucher, Rottweil (DE); Wilhelm Stork, Karlsruhe (DE); Norbert Kraft, Rheinfelden (DE)

(73) Assignee: Metrax GmbH, Rottweil (DE)

( * ) Notice: Subject to any disclaimer, the term of this patent is extended or adjusted under 35 U.S.C. 154(b) by 781 days.

(21) Appl. No.: 12/085,084

(22) PCT Filed: Nov. 15, 2006

(86) PCT No.: PCT/EP2006/010959
§ 371 (c)(1),
(2), (4) Date: Sep. 10, 2008

(87) PCT Pub. No.: WO2007/057169
PCT Pub. Date: May 24, 2007

(65) Prior Publication Data
US 2009/0069857 A1    Mar. 12, 2009

(30) Foreign Application Priority Data
Nov. 15, 2005   (DE) .......................... 10 2005 054 778

(51) Int. Cl.
*A61N 1/39* (2006.01)
(52) U.S. Cl. ............................... 607/6; 607/5
(58) Field of Classification Search .................. None
See application file for complete search history.

(56) References Cited

U.S. PATENT DOCUMENTS

| | | | |
|---|---|---|---|
| 4,088,138 A | 5/1978 | Diack et al. | |
| 4,210,149 A * | 7/1980 | Heilman et al. ................ | 607/5 |
| 4,576,170 A | 3/1986 | Bradley et al. | |
| 4,610,254 A | 9/1986 | Morgan et al. | |
| 4,928,690 A * | 5/1990 | Heilman et al. ................ | 607/4 |
| 5,342,404 A | 8/1994 | Alt et al. | |
| 5,720,770 A * | 2/1998 | Nappholz et al. ............... | 607/30 |
| 6,480,734 B1 * | 11/2002 | Zhang et al. ................... | 600/518 |
| 6,694,186 B2 * | 2/2004 | Bardy .............................. | 607/3 |
| 7,899,545 B2 * | 3/2011 | John ............................... | 607/60 |
| 2002/0103508 A1 | 8/2002 | Mathur | |
| 2003/0004547 A1 | 1/2003 | Owen et al. | |
| 2003/0216787 A1 * | 11/2003 | Worden ........................... | 607/5 |
| 2004/0044370 A1 * | 3/2004 | Benser et al. ................... | 607/5 |
| 2004/0215247 A1 * | 10/2004 | Bolz .............................. | 607/7 |

(Continued)

FOREIGN PATENT DOCUMENTS

DE    689 27 898 T2    10/1997

(Continued)

OTHER PUBLICATIONS

"Sudden Death from Cardiac Arrest—Statistics", American Heart Association, americanheart.org, 2004.*

(Continued)

*Primary Examiner* — Kennedy Schaetzle
(74) *Attorney, Agent, or Firm* — Pauley Petersen & Erickson

(57) ABSTRACT

An external automatic defibrillator including an attachment device that can be externally attached and carried by a patient, an identification device for detecting an abnormal event in the cardiac activity, which can be treated by an electric shock, as well as a defibrillator allowing to exert a shock upon the patient after having detected the abnormal event. In order to ensure reliable functioning over a longer period of time, the identification device is configured so that the identification device can detect an abnormal event in an interval of not more than 90 seconds or one minute.

22 Claims, 2 Drawing Sheets

U.S. PATENT DOCUMENTS

| | | | |
|---|---|---|---|
| 2004/0220628 A1* | 11/2004 | Wagner | 607/5 |
| 2005/0085738 A1 | 4/2005 | Stahmann et al. | |
| 2005/0131465 A1 | 6/2005 | Freeman et al. | |
| 2006/0036288 A1* | 2/2006 | Bocek et al. | 607/5 |
| 2008/0081958 A1* | 4/2008 | Denison et al. | 600/300 |
| 2011/0022105 A9* | 1/2011 | Owen et al. | 607/5 |

FOREIGN PATENT DOCUMENTS

| | | |
|---|---|---|
| WO | WO 2004/054656 A1 | 7/2004 |

OTHER PUBLICATIONS

Co-Pending U.S. Appl. No. 10/535,599, filed May 19, 2005; inventor Heinz Bucher; title Defibrillator With Improved Output Stage.

Co-Pending U.S. Appl. No. 10/535,592, filed May 19, 2005; inventor Heinz Bucher; title Defibrillator Comprising a Relay Testing Device.

Co-Pending U.S. Appl. No. 10/540,233, filed Jun. 21, 2005; inventor Jurgen Bucher; title Defibrillator.

* cited by examiner

EXTERNAL AUTOMATIC DEFIBRILLATOR

BACKGROUND OF THE INVENTION

1. Field of the Invention

This invention relates to an automatic external defibrillation device, having an attachment device for external placement on and wear by a patient, having an identification arrangement for detecting an abnormal event in connection with a cardiac activity which is treatable by electric shock, and having a defibrillation arrangement for applying a shock to a patient after the abnormal event has been detected.

2. Discussion of Related Art

An automatic external defibrillation device of this type is disclosed in German Patent Reference DE 689 27 898 T2. An attachment device with an upper body harness or clothing for wearing it, by which an electrode arrangement can be attached to the body of the patient, is provided with this known defibrillation device. A monitoring arrangement is also provided, including at least one monitoring unit on the harness, by which a chest movement during breathing can be detected. A difficulty in connection with such portable automatic external defibrillation devices is in always providing sufficient electrical power for shock treatment.

A similar portable defibrillator, by which the cardiac activity is analyzed and it is determined whether defibrillation is required, is taught by U.S. Pat. No. 4,576,170.

A further portable external defibrillation device is disclosed in United States Patent Application Publication 2003/0004547 A1. The object here is to design the electrodes employed for an extended wearing period.

SUMMARY OF THE INVENTION

One object of this invention is to provide an automatic external defibrillation device of the type mentioned above, but with an increase in functional dependability.

This object is attained by characteristics of this invention as taught in this specification and in the claims. The identification arrangement is designed for detecting an abnormal event within a period of time of at most 90 seconds, or within a minute after the appearance of the event.

The short duration of the period of time for detecting the abnormal event is based on a rapid identification and assures a rapid decision, whether a defibrillation pulse, or sequence of pulses, is required and should be delivered. It has been shown that the shorter the time between ventricular fibrillation and the shock, the less power is required for the shock. The relatively small amount of power for the shock is easier on the heart but it is not necessary to store as much power in the power supply, in particular the battery, for assuring sufficient power for shocking. Thus, it is advantageous if the detection of an abnormal event and treatment take place within one minute.

The further steps are of advantage in connection with gentle treatment and a power-saving operation, so that within this period of time it is possible for the identification arrangement to send an identification signal to the defibrillation device, which can automatically deliver a shock.

Also, steps contribute to the dependable identification of events to be treated, wherein reference data are specified in the identification arrangement for identifying the abnormal event, and an evaluation arrangement is provided, by which the abnormal event can be detected from the patient data regarding the cardiac activity supplied by the identification arrangement, wherein suitable evaluating algorithms in the identification arrangement are made a basis.

In this case, an adjustment to the characteristics and requirements of a respective patient can be provided if the reference data is provided in a patient-specific manner. Here, the patient-specific reference data can be preset by a physician and/or calculated as a function of the respective history in the identification arrangement by specific algorithms.

Dependable data acquisition and evaluation is also supported if an additional sensor arrangement is provided, by which additional information regarding the patient and/or the operational state of the defibrillation device can be made available to the identification arrangement. It is, for example, thus possible to include the actual behavior of the patient and/or to check the positionally-correct application of the electrodes or sensors, and also to monitor the status of the identification arrangement, the defibrillation device and/or the power supply.

Here, advantageous embodiments include that the additional sensor arrangement has at least one movement sensor and/or at least one position sensor, by which a movement or the position of the body can be detected. If during this it is found that the patient moves, the detection of an abnormal event, for example by an EKG, can be discarded as erroneous and a new measurement can be taken. If another person externally moves the body of the patient there would be endangerment by a shock. If, for example, the upper body of the patient is vertical, the detection of an abnormal event could be erroneous, or the patient could fall over after a shock and become injured. In such situations, better differentiations and treatment methods are achieved by the additional information.

In this connection, with advantageous design variations the movement sensor and/or the position sensor can have at least one acceleration sensor.

If the additional sensor arrangement has a strain gauge, it is, for example, possible to dependably detect breathing movements by a suitable algorithm and to include them in the evaluation for detecting an abnormal event.

Furthermore, strong identification criteria for a decision whether a shock should be triggered can be obtained if the additional sensor arrangement has sensors for detecting the neurological state of the patient, sensors for detecting the blinking reflex and/or sensors for detecting eye movement, and if a voice output and/or voice input unit for verbal information from or to a remote control station is provided. The identification arrangement can be designed for detecting and evaluating movements or movement patterns following a request for movement made to the patient and/or for the evaluation of verbal signals from the patient. The identification arrangement can be designed to perform a calibration on the basis of a position and/or movement state of the patient, and the identification arrangement can be designed so that in defined positions of the patient the triggering of the shock is prioritized, or can only be triggered in defined positions.

BRIEF DESCRIPTION OF THE DRAWINGS

This invention is explained in view of exemplary embodiments, making reference to the drawings, wherein.

DETAILED DESCRIPTION OF THE INVENTION

Figure 1:
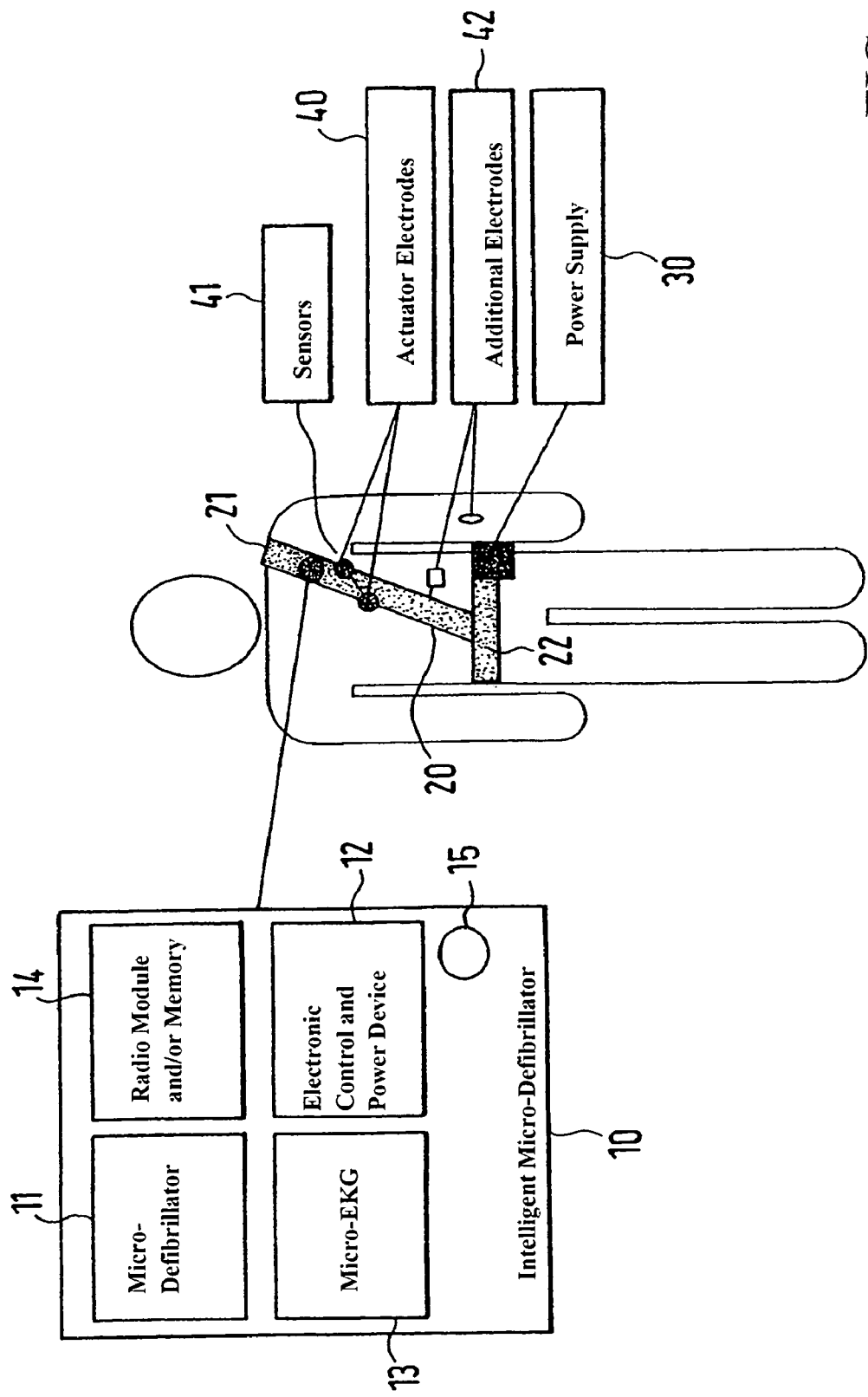
FIG. 1 is a schematic view of a defibrillation device.

FIG. 1 shows an automatic external defibrillation device, which can be permanently placed on the body of a patient in danger of a fatal heart attack and can be worn until the risk falls below a defined threshold.

The mobile defibrillation device, held on the body of a patient by a wearing device 20, has an electronic component 10, a defibrillator component 11, a triggering component 12, a monitoring component 12 and a registration component 14.

The wearing device 20 has, for example, at least one shoulder strap 21 and at least one belt 22 in the form of a chest and/or waist belt. A power supply 30 for the electronic component 10 is maintained on the wearing device 20, in which case the design can be such that the electronic component 10 is placed in a housing together with the power supply 30. Also, actuator electrodes 40, in particular the patient electrodes, as well as further sensors of an additional sensor arrangement 42, if provided, are maintained on the wearing device 20. In this case, the patient electrodes can simultaneously contain sensor units 41, for example in order to perform impedance measurements, and it is possible to detect EKG signals by suitable electrodes, which can also be integrated into the patient electrodes and can be evaluated by the electronic component 10, in a known manner.

Besides an electronic control and power device, in particular for the defibrillator component 11, the electronic component 10 also has a switching component with an identification arrangement for detecting an abnormal event in connection with the cardiac activity of the patient, in which case a computing unit containing suitable algorithms and associated memory devices is provided. The memory device is a part of the registration component 14, which can be designed with a radio module for transmitting and receiving patient data, or data processed in the electronic module 10, to a remote control station. The identification arrangement can have an evaluation arrangement for detecting, from patient data regarding the cardiac activity of the patient, and possibly additional information obtained from an additional sensor arrangement, an abnormal event in the cardiac activity by a comparison with reference data. The reference data, matched to the respective patient, can be stored from the start, and/or can be determined in accordance with a history of the event, possibly adapted, and suitably stored. The patient data are obtained by suitable sensors and are supplied to the identification arrangement via connecting elements and, when required, an identification signal is transmitted by it to the defibrillation device for automatically triggering a shock when needed. Also, previously known patient data, which relate to special, individual characteristics of the patient, can be stored in the electronic component 10, in particular in the identification arrangement, for using them for the detection and evaluation of an abnormal event in the cardiac activity, and to include them in the decision regarding the triggering of a defibrillation shock.

The additional information can, for example, contain movement data or position data regarding the patient, or respiratory activities of the patient, or combinations of these and further data, so that the assurance of detecting the abnormal event can be increased, for example by determining definite movements or movement patterns or, in case of unfavorable conditions, the issue of the identification signal to the defibrillation device can be stopped, or prevented. For example, the additional sensor arrangement 42 has at least one movement sensor and/or at least one position sensor, which are advantageously designed as acceleration sensors, in particular 3D-acceleration sensors, which are advantageously applied at the hip or to the front of the chest. A stretchable tape, with a conductivity that can be changed, and an appropriate algorithm, for example, are suitable for detecting pulmonary activities.

By employing a plurality of movement sensors, it is possible to obtain a more accurate picture of the body activities, and thus to provide a better distinction between active and passive movements. This can occur by evaluating a difference signal, for example, by which movement components acting as common-mode signals from the outside can be recognized as passive movements. Also, placement of the sensors in the appropriately embodied wearing device 20 close to the extremities, for example, can be used for better identifying movements when seated, for example.

In one embodiment of the defibrillation device, there is a voice output and/or input device for voice information from or to a remote control station. With this, the system with the defibrillation device can request the patient to make defined movements and/or changes in body position in case of a questionable signal evaluation. If as a result the system registers a movement or defined characteristic movement patterns, which are identified by the identification arrangement, for example by a comparison with stored movements, or movement patterns, it is possible to assume that a patient is conscious and shows bodily activities, and a shock can be prevented, or a suitable situation can be awaited. With this design, in a further embodiment the patient is requested via the voice input to assume defined body positions and that in these defined body positions a calibration of the system, in particular of the identification arrangement, is performed. In a further embodiment, prior to assuming defined body positions which favor a shock indication, for example lying during sleep, the patient tells this to the defibrillation device via an input unit, so that the signal evaluation can be modified, for example by a change of weight factors in the computer evaluation of the signals.

In a further embodiment, the patient can actively suppress the administration of a shock by pushing operating keys. The preparation of a shock can be signaled by various signals, such as optical, acoustic, and tactile.

In a further embodiment additional sensors are provided, by which it is possible to draw conclusions regarding the neurological state of the patient. For example, the further additional sensors are designed for the generation of evoked potentials, which are generated by signal sources designed for this and are detected via sensor elements. In a further embodiment, checking a blinking reflex and/or eye movements by further additional sensors, wherein in one embodiment can be an electro-oculogram.

Figure 2:
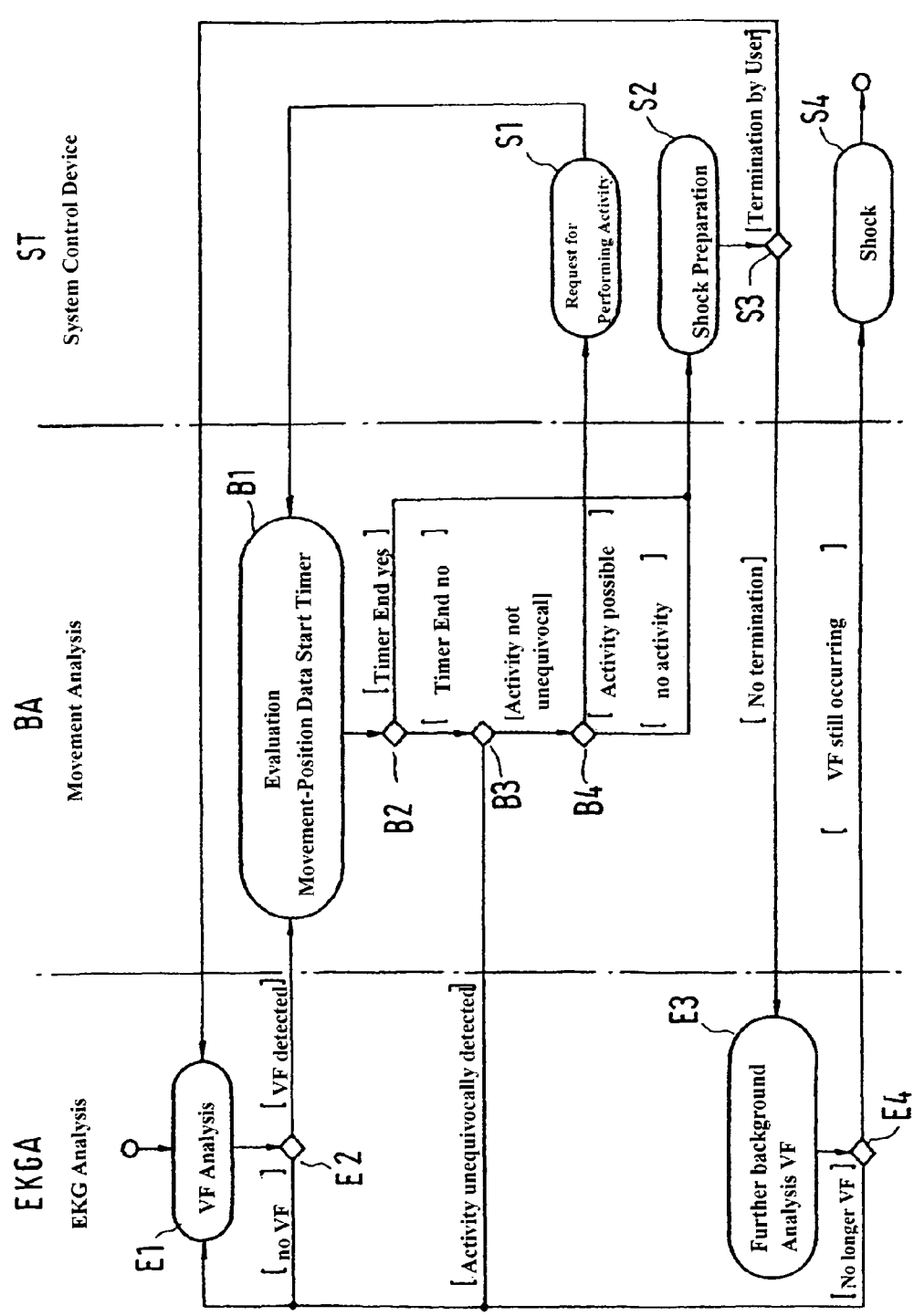
FIG. 2 shows an exemplary embodiment of an analysis and progress control device.

An example for an analysis and progress control device for checking whether a shock should be triggered and whether a shock is possibly required is represented in FIG. 2. The control is represented by the use of action diagrams, divided into an area EKGA for EKG analysis, a movement analysis AB and a system control device ST.

In the EKG analysis EKGA, a check is made in a step E1 starting from an initial point, whether ventricular fibrillation (VF) exists. If in a step E2 it is decided that there is no ventricular fibrillation, a return to step E1 for the analysis of the ventricular fibrillation is made. If it is decided in this step E2 that a ventricular fibrillation has been detected, in a step B1 an evaluation of the movement/position data is performed in the area of the movement analysis BA and a time-measuring device or timer is started for a defined length of time. If in a succeeding step B2 of the movement analysis BA the end of the period of time is determined, a transition is made to a step S2 in the area of the system control device ST for preparing a shock. If it is determined in step B2, that the length of time has not yet expired, a check is made in the area of the movement analysis BA in a succeeding step B3 whether an action by the patient has been identified, which the patient had been previously requested to perform in a step S1, for example acoustically, for example via the above mentioned voice input, visually or by tactile means. If in step B3 an action had been unequivocally detected, a return is made to step B1 of a ventricular fibrillation analysis. If an action is not unequivocally determined in step B3, a determination is made in a further step B4 of the movement analysis whether or not an action is possible. If an action is possible, a transition is made to step S1 in the area of the system control device ST for requesting the action. If it is determined in step B4 that no action can be detected, or is possible, a transition is made to step S2 in the area of the system control device ST for making preparations for a shock. If it is determined in a succeeding step S3 in the area of the system control device ST that the user has terminated the shock preparation, for example by inputting appropriate first information, as discussed above, a return is made to the step E1 of ventricular fibrillation analysis in the area EKGA of the EKG analysis. If no termination is detected in step S3, a transition is made to a step E3 of a further background analysis of the ventricular fibrillation in the area EKGA of the EKG analysis. If it is determined in a successive step E4 that ventricular fibrillation no longer exists, a return is made to step E1 of ventricular fibrillation analysis. If it is determined in step E4 that ventricular fibrillation continues to exist, a shock is triggered in a step S4 in the area of the system control device ST. After that, a transition is made to an end point, after which further activities, such as analyses and checks, can be performed.

In other words, the progress of an analysis by a combination of an EKG and a movement analysis corresponding to the action diagrams in accordance with FIG. 2 can be represented as follows.

a) Request to Perform the Action

The patient is requested, for example visually, acoustically or in a tactile manner, to perform a bodily action, which can be based on a previously specified movement pattern, for example. The incoming transition then includes making a switch from the appropriate decision node B4, provided that an action is possible, to step S1 of the request to perform an action. The resulting transition is that a switch is made from step S1 to step B1 of evaluating the movement/position data and starting the timer.

b) Evaluating the Movement/Position Data and Starting the Timer

In case there is a request made of the patient to show a bodily action, the timer is started for a defined length of time, a time window, in which the action must take place. In this case, incoming transitions are that a switch is made from the decision node E2 to the evaluation, movement/position data, starting the timer, in step B1, provided, that ventricular fibrillation had been detected. Furthermore, a switch is made from the step of requesting the performance of an action to step B1 of evaluating the movement/position data and starting the timer. The incoming transition here is the shift from step B1 to the decision node B2.

c) Shock

A shock is applied here, and the analysis is freshly started thereafter. An incoming transition here is the switch from the decision node E4 to step S4, provided that ventricular fibrillation still exists. An outgoing transition includes the switch from step S4 shock to the end point.

d) Shock Preparation

Part of a shock preparation are the notice to the patient and the surroundings by visual, acoustical and/or tactile signals, charging of the capacitor unit of the defibrillator and dispensing of a gel in the defibrillator electrodes. Incoming transitions here are a switch from the decision node B4 for shock preparation in accordance with step S2, provided no actions are noted, and from the decision node B2 for shock preparation in step S2, provided that the length of time has ended. An outgoing transition includes the shift from shock preparation in step S2 to the decision node S3.

e) VF-Analysis

Here, an EKG analysis is performed with the goal of detecting ventricular fibrillation. Incoming transitions here are the switch from the initial point to the VF-analysis in step E1, the switch from the decision node E2 back to the VF-analysis, provided that an action by the patient had been unequivocably detected, the switch from the decision node S3 to the VF-analysis E1, provided a termination by the user exists, and the switch from the decision node E4 to the VF-analysis E1, provided ventricular fibrillation no longer exists. An outgoing transition includes a shift made from step E1 of the VF-analysis to the decision node E2.

f) Further Background Analysis VF

The VF background analysis in step E3 continues permanently, even if movement data etc., are evaluated. This analysis is used as a permanent safeguard that a rhythm requiring a shock continues to be present. Here, the incoming transition is the shift from the decision node S3 to the further background analysis in accordance with step E3, provided that no termination was performed by the patient. The outgoing transition here is the shift from the further background analysis E3 to the decision node E4.

In one embodiment of the defibrillation device, the identification arrangement is designed for rapid evaluation and identification of an abnormal event in the cardiac activity, and the defibrillation device is designed for a correspondingly rapid reaction and issuance of a defibrillation pulse. The above mentioned measures are used for rapid and dependable evaluation and identification, in particular, the identification lies within a time period which is shorter than 2 minutes, preferably less than 90 seconds, and even better lies below 1 minute. It has been shown that the shorter the time from the appearance of ventricular fibrillation to the shock is, the less energy is required for the shock. This is easy on the patient, and also does not require as much power, so that the power supply can assure sufficient shocking power over a longer period of time.

The invention claimed is:

1. An automatic external defibrillation device, having an attachment device for an external placement on and wear by a patient, having an identification arrangement for detecting an abnormal event in connection with a cardiac activity, which is treatable by an electric shock, and having a defibrillation arrangement for applying a shock to the patient after the abnormal event has been detected, the defibrillation device comprising:

the identification arrangement designed for detecting an abnormal event within a period of time of at most 90 seconds or one minute, for the identification arrangement to send an identification signal to the defibrillation device within the period of time the defibrillation device can automatically deliver a shock, reference data specified in the identification arrangement for identifying the abnormal event, an evaluation arrangement detecting the abnormal event from the patient data regarding cardiac activity supplied by the identification arrangement, the reference data provided in a patient-specific manner, an additional sensor arrangement (42) making available additional information regarding the patient and/or the operational state of the defibrillation device to the identification arrangement and the additional sensor arrangement (42) having sensors for detecting a neurological state of the patient, sensors for detecting a blinking reflex, and/or sensors for detecting eye movement.

2. The defibrillation device in accordance with claim 1, wherein the additional sensor arrangement (42) has at least one movement sensor and/or at least one position sensor by which a movement or a position of the body can be detected.

3. The defibrillation device in accordance with claim 2, wherein the movement sensor and/or the position sensor has an acceleration sensor.

4. The defibrillation device in accordance with claim 3, wherein the additional sensor arrangement (42) has a strain gauge.

5. The defibrillation device in accordance with claim 2, wherein the additional sensor arrangement (42) has a strain gauge.

6. The defibrillation device in accordance with claim 2, wherein the identification arrangement is designed so that in defined positions of the patient a triggering of the shock is prioritized, or can only be triggered in defined positions.

7. The defibrillation device in accordance with claim 1, wherein a voice output and/or voice input unit (15) for verbal information from or to a remote control station is provided, and the identification arrangement is designed for detecting and evaluating movements or movement patterns following a request for movement made to the patient, and/or for the evaluation of verbal signals from the patient.

8. An automatic external defibrillation device, having an attachment device for an external placement on and wear by a patient, having an identification arrangement for detecting an abnormal event in connection with a cardiac activity, which is treatable by an electric shock, and having a defibrillation arrangement for applying a shock to the patient after the abnormal event has been detected, the defibrillation device comprising:

the identification arrangement designed for detecting an abnormal event within a period of time of at most 90 seconds or one minute, a voice output and/or voice input unit (15) for verbal information from or to a remote control station being provided, and the identification arrangement designed for detecting and evaluating movements or movement patterns following a request for movement made to the patient, and/or for the evaluation of verbal signals from the patient, and the identification arrangement designed to perform a calibration on a basis of a position and/or a movement state taken by the patient.

9. The defibrillation device in accordance with claim 8, wherein for the identification arrangement to send an identification signal to the defibrillation device within the period of time, the defibrillation device can automatically deliver a shock.

10. The defibrillation device in accordance with claim 9, wherein reference data are specified in the identification arrangement for identifying the abnormal event, and an evaluation arrangement detects the abnormal event from the patient data regarding cardiac activity supplied by the identification arrangement.

11. The defibrillation device in accordance with claim 10, wherein the reference data is provided in a patient-specific manner.

12. The defibrillation device in accordance with claim 11, wherein an additional sensor arrangement (42) makes available additional information regarding the patient and/or the operational state of the defibrillation device to the identification arrangement.

13. The defibrillation device in accordance with claim 12, wherein the additional sensor arrangement (42) has sensors for detecting a neurological state of the patient, sensors for detecting the blinking reflex, and/or sensors for detecting eye movement.

14. The defibrillation device in accordance with claim 8, wherein the additional sensor arrangement (42) has sensors for detecting a neurological state of the patient, sensors for detecting the blinking reflex, and/or sensors for detecting eye movement.

15. The defibrillation device in accordance with claim 14, wherein a voice output and/or voice input unit (15) for verbal information from or to a remote control station is provided, and the identification arrangement is designed for detecting and evaluating movements or movement patterns following a request for movement made to the patient, and/or for the evaluation of verbal signals from the patient.

16. The defibrillation device in accordance with claim 15, wherein the identification arrangement is designed to perform a calibration on a basis of a position and/or a movement state taken by the patient.

17. The defibrillation device in accordance with claim 16, wherein the identification arrangement is designed so that in defined positions of the patient a triggering of the shock is prioritized, or can only be triggered in defined positions.

18. The defibrillation device in accordance with claim 8, wherein reference data are specified in the identification arrangement for identifying the abnormal event, and an evaluation arrangement detects the abnormal event from the patient data regarding cardiac activity supplied by the identification arrangement.

19. The defibrillation device in accordance with claim 18, wherein the reference data is provided in a patient-specific manner.

20. The defibrillation device in accordance with claim 8, wherein an additional sensor arrangement (42) makes available additional information regarding the patient and/or the operational state of the defibrillation device to the identification arrangement.

21. The defibrillation device in accordance with claim 20, wherein the additional sensor arrangement (42) has at least one movement sensor and/or at least one position sensor by which a movement or a position of the body can be detected.

22. The defibrillation device in accordance with claim 21, wherein the movement sensor and/or the position sensor has an acceleration sensor.

* * * * *